(12) United States Patent
Van Neste et al.

(10) Patent No.: US 7,961,313 B2
(45) Date of Patent: Jun. 14, 2011

(54) PHOTOACOUSTIC POINT SPECTROSCOPY

(75) Inventors: Charles W. Van Neste, Kingston, TN (US); Lawrence R. Senesac, Knoxville, TN (US); Thomas G. Thundat, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 282 days.

(21) Appl. No.: 12/189,652

(22) Filed: Aug. 11, 2008

(65) Prior Publication Data

US 2010/0033722 A1 Feb. 11, 2010

(51) Int. Cl.
*G01J 3/30* (2006.01)
(52) U.S. Cl. ........................................... 356/311
(58) Field of Classification Search .................. 356/402, 356/432, 337, 311; 73/643, 601
See application file for complete search history.

(56) References Cited

U.S. PATENT DOCUMENTS

| | | | |
|---|---|---|---|
| 4,255,971 A | | 3/1981 | Rosencwaig |
| 4,276,780 A | | 7/1981 | Patel et al. |
| 4,543,486 A | * | 9/1985 | Rose ........................ 250/492.1 |
| 4,678,905 A | * | 7/1987 | Phillips ................... 250/227.21 |
| 4,897,541 A | * | 1/1990 | Phillips ................... 250/227.21 |
| 4,931,384 A | | 6/1990 | Layton et al. |
| 5,036,708 A | | 8/1991 | Urban et al. |
| 5,141,331 A | | 8/1992 | Oehler et al. |
| 5,285,677 A | | 2/1994 | Oehler |
| 5,319,977 A | | 6/1994 | Quate et al. |
| 5,360,268 A | | 11/1994 | Hayashi et al. |
| 5,391,001 A | | 2/1995 | Rupert et al. |
| 5,440,388 A | | 8/1995 | Erickson |
| 5,977,538 A | * | 11/1999 | Unger et al. ............... 250/227.2 |
| 6,006,593 A | * | 12/1999 | Yamanaka ...................... 73/105 |
| 6,400,449 B2 | | 6/2002 | Maris et al. |
| 6,466,806 B1 | | 10/2002 | Geva et al. |
| 6,639,184 B1 | | 10/2003 | Ennis |
| 6,657,196 B2 | | 12/2003 | Endo et al. |
| 6,831,747 B2 | | 12/2004 | Ferrell et al. |
| 7,207,206 B2 | | 4/2007 | Pinnaduwage et al. |

(Continued)

FOREIGN PATENT DOCUMENTS

DE 39 25 312 A1 4/1990

(Continued)

OTHER PUBLICATIONS

PCT Seach Report and Written Opinion dated Feb. 6, 2010, PCT/US2009/052820, filed May 8, 2009.

(Continued)

*Primary Examiner* — Tarifur R. Chowdhury
*Assistant Examiner* — Isiaka O Akanbi
(74) *Attorney, Agent, or Firm* — Brinks Hofer Gilosn & Lione

(57) ABSTRACT

A system and method are disclosed for generating a photoacoustic spectrum in an open or closed environment with reduced noise. A source may emit a beam to a target substance coated on a detector that measures acoustic waves generated as a result of a light beam being absorbed by the target substance. By emitting a chopped/pulsed light beam to the target substance on the detector, it may be possible to determine the target's optical absorbance as the wavelength of light is changed. Rejection may decrease the intensity of the acoustic waves on the detector while absorption may increase the intensity. Accordingly, an identifying spectrum of the target may be made with the intensity variation of the detector as a function of illuminating wavelength.

20 Claims, 4 Drawing Sheets

U.S. PATENT DOCUMENTS

| | | | |
|---|---|---|---|
| 7,243,548 | B2 | 7/2007 | Thundat et al. |
| 7,245,380 | B2 | 7/2007 | Kosterev |
| 7,326,580 | B2 | 2/2008 | Fukushima et al. |
| 7,411,189 | B2 | 8/2008 | Kawakatsu |
| 7,442,922 | B2 | 10/2008 | Knebel et al. |
| 7,448,269 | B2 | 11/2008 | Shekhawat et al. |
| 7,605,922 | B2 | 10/2009 | Willing et al. |
| 7,665,364 | B2 * | 2/2010 | Su et al. .................... 73/643 |
| 7,691,583 | B2 | 4/2010 | Craighead |
| 2004/0085540 | A1 | 5/2004 | Lapotko et al. |
| 2004/0120577 | A1 | 6/2004 | Touzov |
| 2005/0070803 | A1 | 3/2005 | Cullum et al. |
| 2005/0117155 | A1 | 6/2005 | Kosterev |
| 2005/0201661 | A1 | 9/2005 | Loock et al. |
| 2005/0244747 | A1 | 11/2005 | Nagai et al. |
| 2007/0175760 | A1 | 8/2007 | Thundat et al. |
| 2007/0220978 | A1 | 9/2007 | Su et al. |
| 2007/0220979 | A1 | 9/2007 | Su et al. |
| 2008/0094614 | A1 | 4/2008 | Tuschel et al. |
| 2008/0276695 | A1 | 11/2008 | Prater et al. |
| 2009/0174884 | A1 | 7/2009 | Kosterev et al. |
| 2009/0321647 | A1 | 12/2009 | Shelley et al. |

FOREIGN PATENT DOCUMENTS

| | | |
|---|---|---|
| EP | 1 493 380 A1 | 1/2005 |
| JP | 11253794 A | 9/1999 |
| JP | 2001183294 A | 7/2001 |

OTHER PUBLICATIONS

C.W. Van Neste, L.R. Senesac, and T. Thundat, Standoff Detection of Explosive Residues Using Photothermal Microcantilevers, *Applied Physics Letters*, 92, 134102 (2008), © 2008 American Institute of Physics.

ORNL Demonstrates Super-Sensitive Explosives Detector, Oakridger.com, Jun. 30, 2008.

Waghe, A., Kanan, S.M., Abu-Yousef, I., Jensen, B., and Tripp, C., Infrared Study of UV-Irradiated Tungsten Trioxide Powders Containing Adsorbed Dimethyl Methyl Phosphonate and Trimethyl phosphate, *Res. Chem Intermed*, vol. 32, No. 7, pp. 613-623, 2006.

Yang, P.W. and Casal, H.L., In Situ Diffuse Reflectance Infrared Spectroscopic Study of the Photodecomposition of Dibenzyl Ketone Adsorbed on Zeolites, *J. Phys. Chem*, 90, pp. 2422-2424, 1986.

PCT Seach Report and Written Opinion dated Dec. 14, 2009, PCT/US2009/052806, filed Aug. 5, 2009.

Uotila, J, *A new design of the differential photoacoustic gas detector combined with a cantilever microphone*, The European Physical Journal, Special Topics, vol. 153, Mar. 12, 2008, pp. 401-404.

Koskinen, V. et al., *Cantilever enhanced photoacoustic detection of carbon dioxide using a tunable diode laser source*, Applied Physics B, Lasers and Optics, vol. 86, No. 3, Jan. 23, 2007, pp. 451-454.

Kosterev, A. et al., *Applications of quartz tuning forks in spectroscopic gas sensing*, Review of Scientific Instruments, vol. 76, No. 4, Mar. 23, 2005, pp. 043105-1 043105-9.

Su, X. et al., *Quartz tuning fork biosensor*, Biosensors and Bioelectronics, Elsevier, vol. 17, No. 1/02, Jan. 1, 2001, pp. 111-117.

C.W. Van Neste, L.R. Senesac, and T. Thundat, Standoff Photoacoustic Spectroscopy, *Applied Physics Letters*, 92, 234102 (2008), © 2008 American Institute of Physics.

Uotila, J and Kauppinen, Jyrki; *Fourier Transform Infrared Measurement of Solid-, Liquid-, and Gas-Phase Samples with a Single Photoacoustic Cell*; Applied Spectroscopy; vol. 62, No. 6; 2008; pp. 655-659.

Sievilia, P., Rytkonen, V-P, Hahtela, O, Chekurov, N., Kauppinen, J., Tittonen, I.; *Fabrication and characterization of an ultrasensitive acousto-optical cantilever*; Journal of Micromechanics and Microengineering; 17; 2007; pp. 852-859.

Lindley, R.E., Parkes, A.M., Keen, K.A., McNaghten, E.D., Orr-Ewing, A.J., *A sensitivity comparison of three photoacoustic cells containing a single microphone, a differential dual microphone or a cantilever pressure sensor*; Applied Physics B, Lasers and Optics; 86; 2007; pp. 707-713.

Koskinen, V., Fonsen, J., Kauppinen, J., Kauppinen, I., *Extremely sensitive trace gas analysis with modern photoacoustic spectroscopy*; Science Direct, Vibrational Spectroscopy; 42; 2006; pp. 239-242.

Ledermann, N., Muralt, P., Baborowski, J., Forster, M., Pellaux, J-P; *Piezoelectric $Pb(Zr_x, Ti_{1-x})O3$ thin film cantilever and bridge acoustic sensors for miniaturized photoacoustic gas detectors*; Journal of Micromechanics and Microengineering; 14; 2004; pp. 1650-1658.

Wells, P. N. T.; *A Vital Diagnostic Tool that Has Great Opportunities for Further Development*; IEEE Engineering in Medicine and Biology; Sep./Oct. 2000; pp. 14-20.

Crippa, P.R., Vecli, A., Viappiani, C.; *Time-resolved photoacoustic spectroscopy: new developments of an old idea;* New Trends in Photobiology (Invited Review); 24; 1994; pp. 3015.

*XI International Scanning Probe Microscopy Conference 2009—Poster Session*; (8 pages).

Tetard et al., *New modes for subsurface atomic force microscopy through nanomechanical coupling*; Nature Nanotechnology (Letters) (Dec. 20, 2009); www.nature.com/naturenanotechnology.

*Crossing the line: how aggressive cells invade the brain*; R&D Mag Nov. 6, 2009; pp. 1-3; www.rdmag.com/.

Tetard et al., *Elastic phase response of silica nanoparticles buried in soft matter*; Applied Physics Letters 93; 133113 (Published on-line Oct. 2, 2008); pp. 133113-1-133113-3.

*First helium microscope is put through paces at NIST*; R&D Mag (Sep. 3, 2008); pp. 1-2; www.rdmag.com/News/2008/09/First-helium-microscope-is-put-through-paces-at-NIST.

*WITec Microscope Technology Win Prestigious 2008 R&i D 100*; Chemie.De (Jul. 10, 2008); www.chemie.ded/news/e/84528.

*WITec Microscope Technology Wins Prestigious 2008 R&D 100 Award*; WITec; Jul. 2008 www.witec.de/en/company/witecnews/news.php?id=37.

Tetard et al., *Imaging nanoparticles in cells by nanomechanical holography*; Nature Nanotechnology Letters (Jun. 22, 2008); pp. 501-505; www.nature.com/naturenanotechnology.

Wouters, et al., *Automated Scanning Probe Microscopy for Combinatorial Polymer Research*; Mater.Res.Soc.Symp.Proc.vol. 894 (2006), pp. 111-117.

Shekhawat et al., *Nanoscale Imaging of Buried Structures via Scanning Near-Field Ultrasound Holography*; Science Mag; vol. 310; Oct. 7, 2005; www.sciencemag.org; pp. 89-92.

Cuberes et al., *Heterodyne force microscopy of PMMA/rubber nanocomposites: nanomapping of viscoelastic response at ultrasonic frequencies*; J. Phys.D: Appl. Phys. 33 (2000); pp. 2347-2355.

Kolosov et al., *Nonlinear Detection of Ultrasonic Vibrations in an Atomic Force Microscope*; Jpn. J. Appl. Phys. vol. 32 (1993); pp. L 1095-L 1098.

Tetard et al., *New modes for subsurface atomic force microscopy through nanomechanical coupling*; Nature Nanotechnology (Supplementary Information); www.nature.com/naturenanotechnology; pp. 1-9, 20-28.

*AFM-Raman System*; Renishaw; pp. 1-3; http://www.renishaw.com/en/6638.aspx.

*MultiView 1000*; Nanonics Imaging Ltd.; pp. 1-7; http://www.nanonics.co.il/multiview-1000.html.

*Mono Vista CRS*; Princeton Instruments; pp. 1-2; www.princetoninstruments.com/products/specsys/monovistacrs/.

*Alpha500 Automated Confocal Raman & Atomic Force Microscope*; WITec; www.witec.de.

*Alpha300A Atomic Force Microscope*; WITec; www.witec.de.

*Welcome to WITec*; WITec; www.witec-instruments.com/en/home/.

*Atomic Force Microscope alpha300 A*; WITec; www.witec-instruments.com/en/products/afm/alpha300a/.

*Confocal Raman and Atomic Force Microscope alpha 500*; WITec; www.witec-instruments.com/en/products/raman/alpha500/.

*Atomic force microscope*; Wikipedia, the free encyclopedia; pp. 1-7; http://en.wikipedia.org/wiki/Atomic_force_microscope.

*Lock-in Amplifier*; Wikipedia, the free encyclopedia; pp. 1-4 http://en.wikipedia.org/wiki/Lock-in_amplifier.

Google Search results for "mode synthesizing sensing atomic force microscopy", www.google.com/search?hl=en&ie=ISO-8859-1&q=mode+synthesizing+sensing+atomic+force+micro...; (2 pages).

* cited by examiner

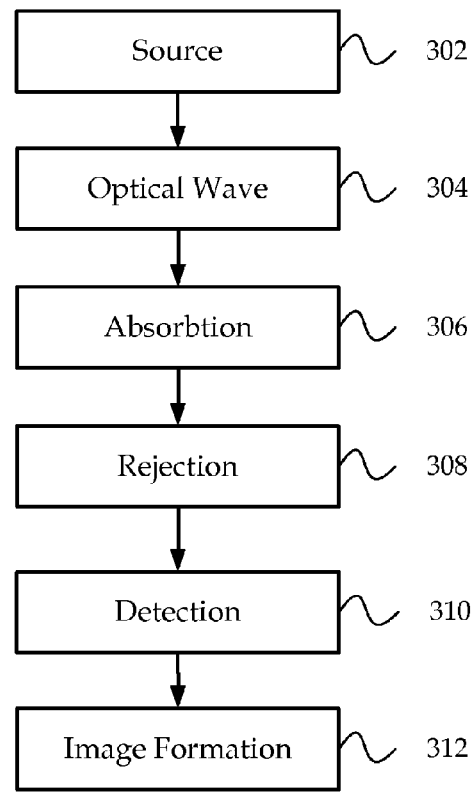
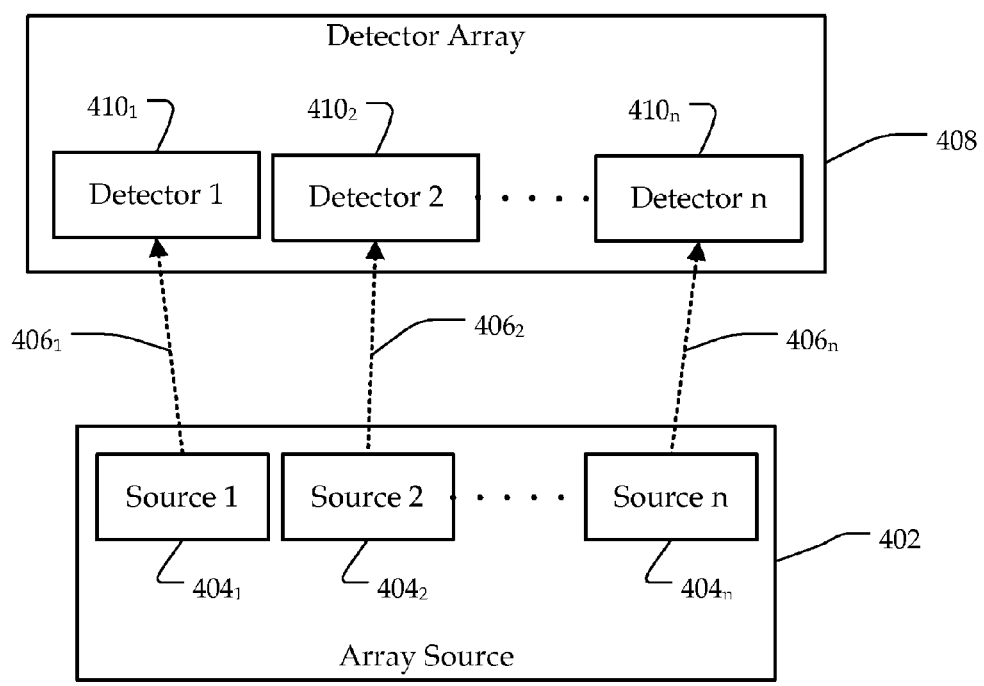

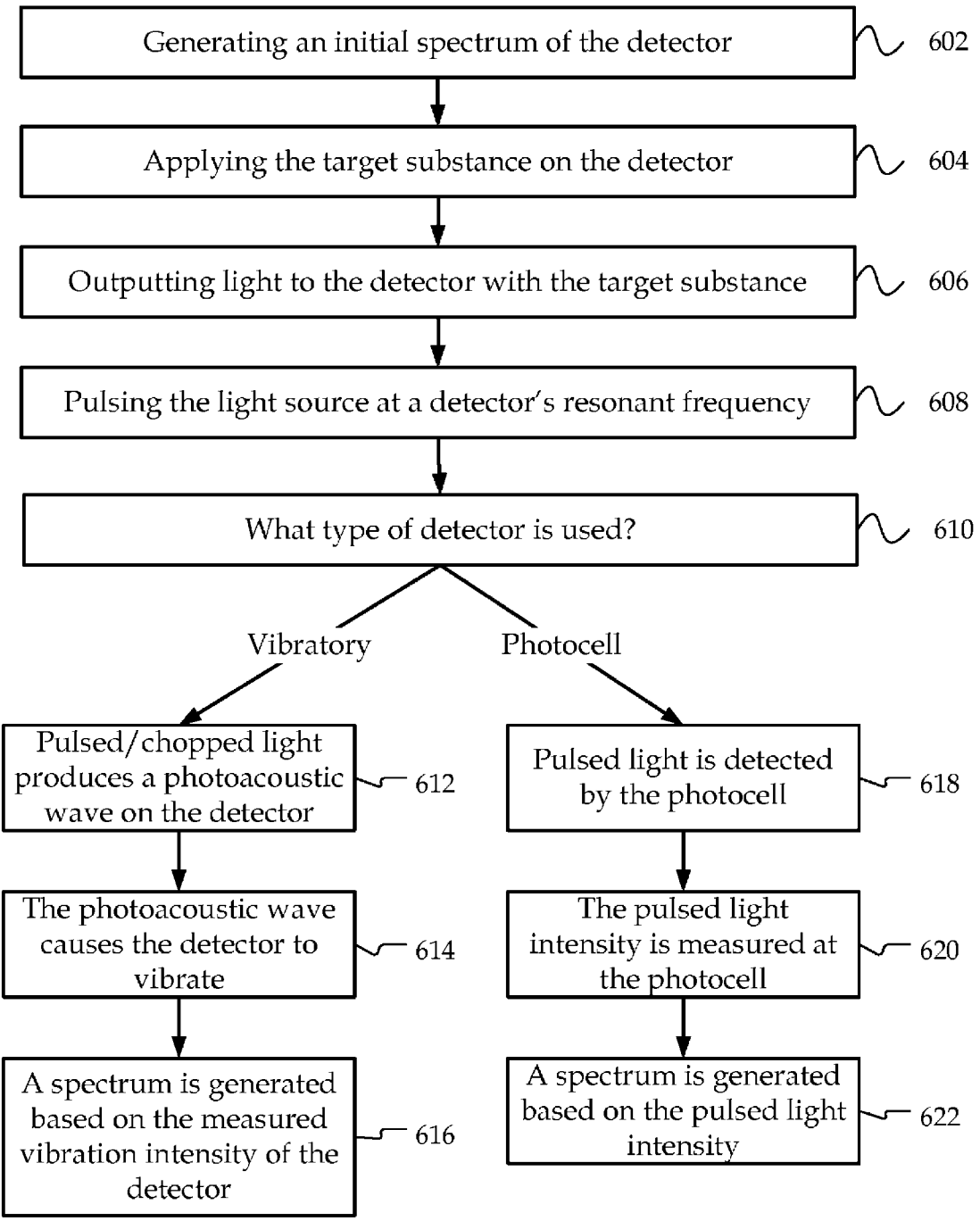

PHOTOACOUSTIC POINT SPECTROSCOPY

STATEMENT REGARDING FEDERALLY SPONSORED RESEARCH

This invention was made with government support under Contract No. DE-AC05-00OR22725 awarded by the U.S. Department of Energy. The government has certain rights in the invention.

RELATED APPLICATION

This application is related to the application entitled "REVERSE PHOTOACOUSTIC STANDOFF SPECTROSCOPY," filed on Aug. 11, 2008, U.S. Ser. No. 12/189,663, now U.S. Pat. No. 7,824,423, which is incorporated by reference.

BACKGROUND

Photoacoustic spectroscopy (PAS) may utilize the photoacoustic effect. The photoacoustic effect may include a conversion between light and acoustic waves due to absorption and localized thermal excitation. Light may be absorbed and transformed into kinetic energy. The absorption may result in local heating and a pressure/sound wave. A measurement of the sound waves at different wavelengths may be used to generate a photoacoustic spectrum of a sample. In an open environment, it may be difficult to detect these waves. The waves may spread and stretch their energy outward and they may be exposed to environmental noise, which may reduce the range and sensitivity for producing a photoacoustic spectrum.

BRIEF DESCRIPTION OF THE DRAWINGS

The system and method may be better understood with reference to the following drawings and description. Non-limiting and non-exhaustive embodiments are described with reference to the following drawings. The components in the drawings are not necessarily to scale, emphasis instead being placed upon illustrating the principles of the invention. In the drawings, like referenced numerals designate corresponding parts throughout the different views.

FIG. 3 illustrates exemplary photoacoustic imaging;
FIG. 4 is spectroscopy system with source and detector arrays;
FIG. 6 illustrates a process for point sensor spectroscopy.

DETAILED DESCRIPTION

By way of introduction, a system and method for generating a photoacoustic spectrum without an enclosed chamber is described. A source may emit a beam to a target and a detector measures signals generated as a result of the beam being emitted on the detector. The detector is coated with a target material, residue, or molecule. By emitting a chopped/pulsed light beam to the target coating on the detector, it may be possible to determine the target's optical absorbance by monitoring the intensity of photoacoustic vibration produced by the light on the detector at different wavelengths. As the wavelength of light is changed, the target may absorb or reject each optical frequency. Rejection may decrease the photoacoustic intensity at the detector and absorption may increase the intensity. Accordingly, an identifying spectrum of the target coating may be made with the photoacoustic wave intensity variation of the detector as a function of illuminating wavelength. The detector may comprise a vibrating or oscillatory sensor and the observed spectrum may correspond with the photoacoustic spectrum of the sample.

Figure 1:
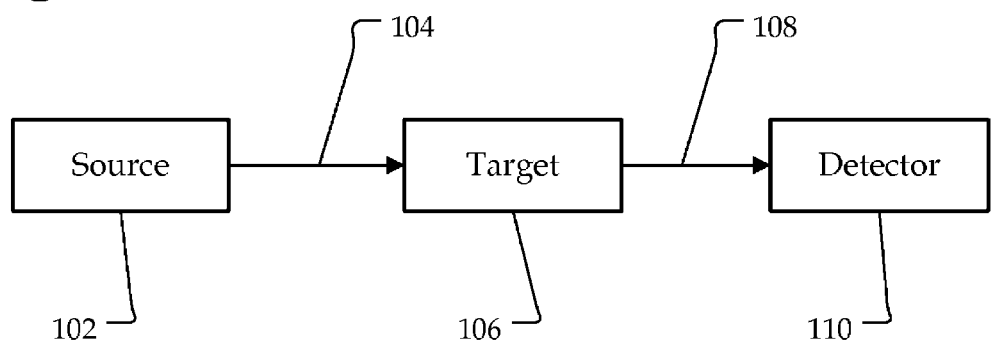
FIG. 1 illustrates an exemplary spectroscopy system.

Photoacoustic spectroscopy may measure the photoacoustic effect on a target substance or material. FIG. 1 illustrates an exemplary photoacoustic spectroscopy system. The spectroscopy system may include a source 102, a target 106, and a detector 110. The source 102 may include a beamformer or a light source, such as a laser, monochromator, light emitting diode (LED), diode laser, LED pile, or the sun with a grating. The source 102 may be tunable.

The source 102 may provide an optical beam 104 to a target substance 106. The optical beam 104 may include a light beam or a laser emission. The light source may be oscillatory, such that the optical beam 104 is chopped or pulsed at a predetermined or adjustable frequency. The target 106 may be a solid, liquid, or gas on or around the detector 110 that is analyzed by the photoacoustic effect. For example, the target 106 may be a residue, such as an explosives or gun powder residue that is to be identified. In one example, the target 106 may be a residue from a surface at an airport that is tested for explosive and/or other material residues that are placed on the detector 110. Alternatively, the target 106 may be human tissue or cells, such that a medical doctor may test for skin cancer or other skin conditions by analyzing a spectrum of a cell placed on the detector 110. The spectra for cancer cells may be different from the spectra for normal cells.

The analysis may identify or determine various properties of the target residue 106. The optical beam 104 may be partially absorbed and/or partially rejected by the target 106 on the detector 110. When the target 106 absorbs the optical beam 104, an acoustic wave 108 is generated on the surface of detector 110. The acoustic wave 108 induces a vibration to the detector 110. The intensity of the acoustic wave 108 is proportional to the wavelength of the optical beam 104. The acoustic wave 108 may produce the maximum vibration of the detector 110 when the pulse frequency of the optical beam 104 matches the resonant frequency of the detector 110.

The detector 110 may be a mechanical resonator that measures an acoustic signal. Acoustic waves may develop on the detector 110 as a result of the pulsed optical beam 104, which are used to generate a photoacoustic spectrum. The intensity and frequency of the acoustic waves may be dependent on the wavelength and intensity of optical beam 104.

The optical beam 104 may produce acoustic waves on the detector's surface as a result of the photoacoustic effect. The detector 110 may be a vibratory detector to measure the pulsed optical beam 104 using the photoacoustic effect generated on the surface of the detector. The intensity of the generated photoacoustic waves on the surface of the detector 110 may be proportional to the intensity of the optical beam 104. The photoacoustic waves 108 produced on the surface of the detector 110 may induce a mechanical vibration of the detector 110. The detector 110 may be coupled with an analysis apparatus, such as a computer system, for analyzing the target 106 through vibration of the detector 110.

Figure 2:
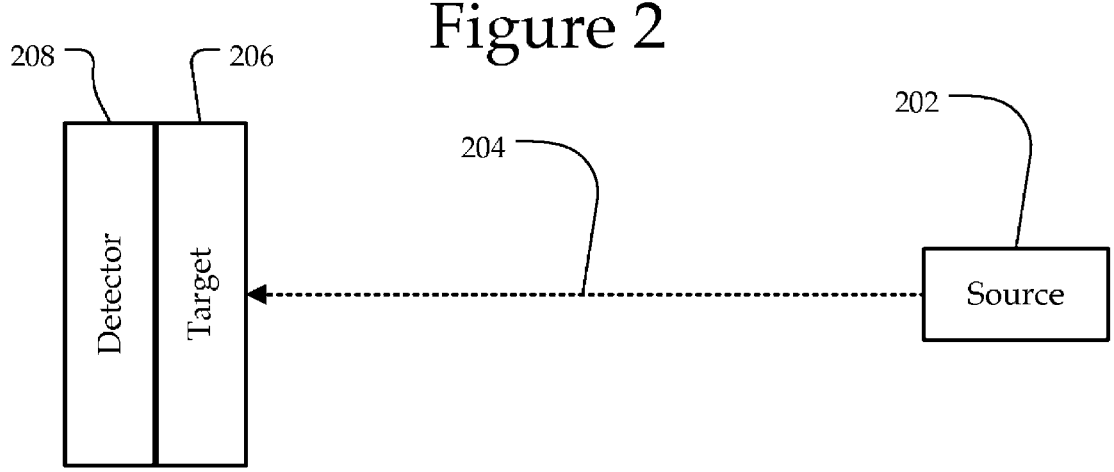
FIG. 2 illustrates an exemplary photoacoustic point spectroscopy system.

FIG. 2 is an alternative embodiment of a remote spectroscopy system 200. The remote spectroscopy system 200 includes a source 202, a target 206, and a detector 208. The source 202 may be a tunable light source, such as a monochromator, tunable laser, light emitting diode (LED), diode laser, or LED pile. The source 202 emits an optical beam 204 at the target 206 and detector 208. The optical beam 204 is chopped or pulsed at a predetermined frequency.

The detector 208 may be coated or covered with the material or substance of the target 206. The detector 208 may be used to identify the molecules of the target 206 by identifying a spectrum based on the target 206. The detector 208 may include the detectors described above. The detector 208 may be vibratory sensor that is coated with molecules of the target 206. The vibratory detector may further include a standard, high-sensitivity microphone, NEMS or MEMS membrane, or a micro-/nano-cantilever beam. The vibratory sensor is excited by photoacoustic waves that may be generated by the optical beam 204. Acoustic waves produced by the pulse/chop frequency of the optical beam 204, mechanically oscillate the vibratory sensor. The chop/pulse of the optical beam 204 produces photoacoustic waves at the air/surface boundary of the sensor which drive the sensor into mechanical oscillation. A photoacoustic spectrum is generated when the absorbed light is coupled to the molecules and used to mechanically excite the sensor. The resonant frequency of the sensor may be dynamically monitored and fed to the pulse/chop mechanism so that the optical beam 204 is pulsated at the resonant frequency of the sensor. The sensor may be placed in/around gasses, pressures, and/or temperatures that improve the maximum signal output of the device.

When the wavelength (color) of the optical beam 204 is changed, the molecules of the target 206 may absorb or reflect more or less of the optical beam 204. The corresponding photoacoustic waves generated by the molecular absorption of the optical beam 204 thus undergo increasing/decreasing amplitude as the optical wavelength is changed. This alters the vibrational amplitude of the detector's mechanical actuator (tine, diaphragm, etc.). An identifying spectrum of the detector 208 and the attached target 206 may be generated based on the vibrational amplitude of the sensor verses the optical wavelength of the optical beam 204. The identifying spectrum may be derived after subtracting out an initial spectrum taken of the detector 208 without the target substance 206.

Alternatively, the detector 208 may comprise a photocell rather than a vibratory detector. An initial spectrum of the photocell detector is recorded without the target 206. The photocell is placed in an environment where molecules of the target 206 attach to the photocell's surface. The spectrum of the photocell with the target 206 is measured and subtracted from the initial spectrum. Characteristics or an identity of the target 206 may be determined by comparing its measured spectra signal with known spectra.

FIG. 3 illustrates exemplary photoacoustic imaging. A source 302 provides an optical wave 304 to a target. The optical wave 304 is pulsed or chopped before being partially or fully absorbed 306 by the target. The pulsing of the optical wave generates an acoustic wave on the detector. Certain frequencies of the optical wave 304 will be absorbed, while other frequencies may be rejected 308 by the target. The target is a substance placed on a detector. As the light is absorbed or rejected, the acoustic wave's amplitude varies on the detector. The detection 310 of the light may be produced by the vibration of the detector by the acoustic waves generated on the detector's surface as in detection 310. The detector's output may be used for forming an image 312. The detection 310 may include an amplification of the measured waves 310. For example, the detection 310 may include the measuring of acoustic waves produced on a microphone diaphragm or a quartz tuning fork tine that generates an acoustic wave on the surface of the microphone diaphragm or a quartz tuning fork tine used to create an image 312. The image formation 312 may be a photoacoustic spectrum of the target that is used to identify that target. As the color of the optical wave 304 is changed, the target will absorb 306 certain wavelengths (i.e. colors) better than others. This may vary the intensity of the optical waves 304 illuminated on the detector, which in turn may vary the acoustic waves generated at the detection 310.

FIG. 4 is an alternative photoacoustic point spectroscopy system with source and detector arrays. The system may include an array source 402, and a detector array 408. The array source 402 may include a plurality of sources 404, such as a first source $404_1$, a second source $404_2$, and additional sources up to an $n^{th}$ source $404_n$. The value of n may be any integer greater than or equal to one. Each of the sources 404 may represent a different light source and/or a different color (wavelength) of emitted light. In particular, the first source $404_1$ emits a first light beam $406_1$, a second source $404_2$ emits a second light beam $406_2$, and an $n^{th}$ source $404_n$ emits an nth light beam $406_n$. In an alternative embodiment, the light beams 406 may be emitted as a single light beam. The n light beams 406 may each have a different wavelength that correspond with the detectors 410 in the detector array 408. In particular, the first light beam $406_1$ is received by the first detector $410_1$, the second light beam $406_2$ is received by the second detector $410_2$, and the $n^{th}$ light beam $406_n$ is received by the $n^{th}$ detector $410_n$. The detectors 410 may have different resonant frequencies. Each of the sources 404 may be pulsed/chopped at a frequency that matches a resonant frequency of the corresponding detector 410.

The detector array 408 and/or the detectors 410 may be coated or covered with a target substance or target material (not shown). The detectors 410 may be used to identify the molecules of the target substance by identifying a spectrum based on the target substance. As described with respect to FIG. 1, the detectors 410 may be vibratory detectors that are used to generate a spectrum based on the light beams 406 that are emitted onto the detectors 408 and the target substance producing an acoustic wave that sets the detectors 408 into vibration. The emission of beams 406 of different wavelengths by each of the sources 404 from the array source 402 may occur substantially simultaneously, which may reduce the time needed to scan from one end of the spectral range to the other with a single source. Accordingly, an analysis of the target substance over a wide spectral range may be expedited when an array of sources and detectors are used.

Figure 5:
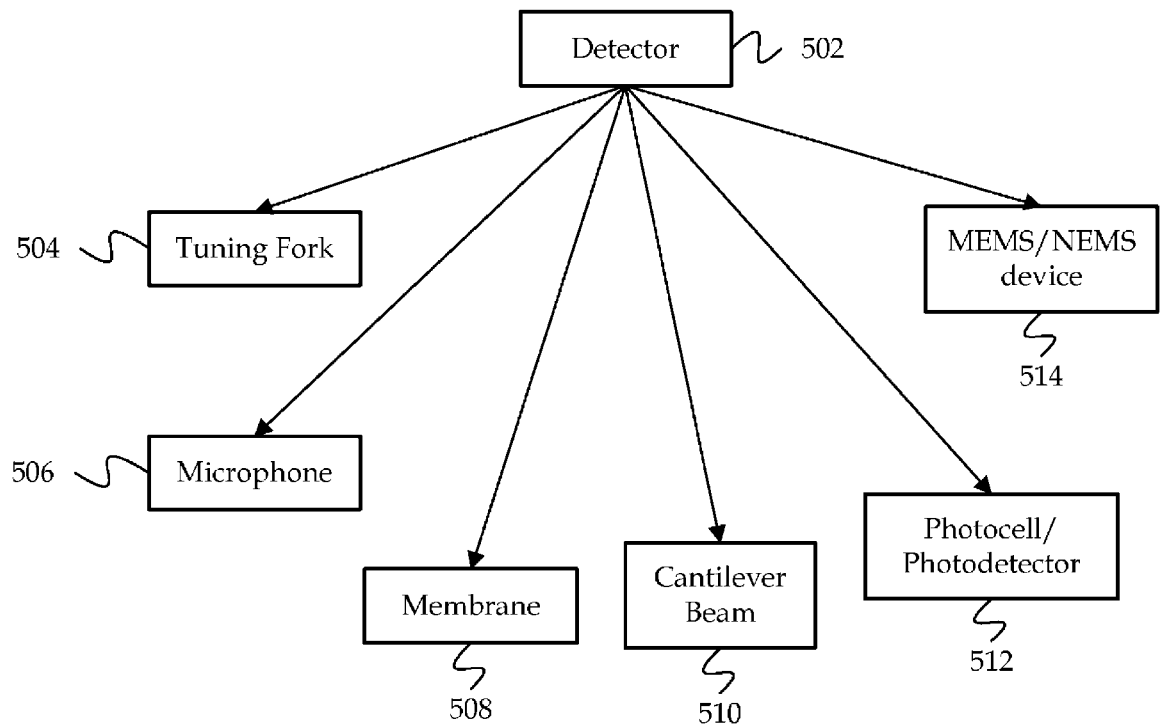
FIG. 5 illustrates exemplary detectors.

FIG. 5 illustrates exemplary detectors. The detector 110 and the detectors 410 may comprise the detector 502 and/or the detection 210 may be performed by the detector 502. The detector 502 may comprise a tuning fork 504, microphone 506, membrane 508, cantilever beam 510, microelectromechanical system (MEMS) device 512, and/or nanoelectromechanical system (NEMS) device 514.

The tuning fork 504 may comprise a tuning fork made of any material, such as quartz. An exemplary quartz crystal tuning fork, such as those manufactured for wrist watches, may be used. An exemplary quartz crystal tuning fork may be quoted by the manufacturer as having a quality factor near 90,000 in a vacuum. In air, quartz crystal tuning forks may produce a sensitivity on the order of about 0.1 Hz. When pulsed light is allowed to hit one of the tines of the tuning fork, a photoacoustic pressure may develop at the air-surface interface. When the frequency of pulsed light is close to the resonant frequency of the tuning fork, an increased piezoelectric signal may be generated due to the piezoelectric material nature of quartz. A quartz crystal tuning fork resonator may benefit from sharp resonant peaks, lower purchasing cost, and a pulsed or chopped optical stimulation range from any optical frequency, including but not limited to ultraviolet (UV) through far infrared (IR).

The microphone 506 may be any microphone utilized to measure acoustic waves generated on the surface of the microphone's diaphragm as a result of the pulsed or chopped scattered light. Alternatively, the microphone 506 may be any acoustic transducer configured to measure acoustic waves. Likewise, the membrane 508, such as a NEMS or MEMS membrane, and the cantilever beam 510, such as a micro- or nano-cantilever beam may measure the acoustic waves.

The detector 502 may comprise a photocell 512 or a photodetector. The photocell 512 may measure the intensity of light directly. The photocell 512 may count photons to determine the amount of energy at each wavelength of light that it measures. Accordingly, as the target absorbs or rejects various optical wavelengths, the intensity of the light scattering off the target may change. The photocell 512 detects the intensity changes and produces a voltage accordingly. A spectrum of the target is produced as a function of the outputted photocell voltage and the optical wavelength of the optical beam from the source. The photocell 512 may include AC circuits for measuring oscillation, such as a pulsed source. Alternatively, the detector 502 may comprise any optical detector that measures changes in the light scattered by the target.

Alternatively, the detector 502 may comprise a NEMS/MEMS device 514 that may be any acoustic transducer fabricated to micrometer dimensions which may use other methods of sensing besides membranes and cantilevers. Likewise, the NEMS/MEMS device 514 may be any acoustic transducer fabricated to nanometer dimensions which may use other methods of sensing besides membranes and cantilevers.

FIG. 6 is an exemplary process for photoacoustic point spectroscopy. In block 602, an initial spectrum of the detector is generated. The initial spectrum measures the detector without a target substance. In block 604, the target substance is applied to the detector. In block 606, light is outputted to the detector with the target substance. One or more light sources provide one or more light beams to the detector and target substance. The light beams that are emitted at the detector and target are pulsed at approximately the detector's resonant frequency as in block 608. When an array of sources are used, each of the sources may be pulsed to correspond with the resonant frequency of a corresponding detector in a detector array.

Different types of detectors may measure or react to the incoming light. When a vibratory or oscillatory detector is used in block 610, the pulsed light emitted on the vibratory detector may produce an acoustic wave on the surface of the vibratory detector in block 612. The photoacoustic wave may cause the detector to vibrate in block 614. A spectrum may be generated based on the measured intensity change of the photoacoustic induced vibration of the detector for different wavelengths of emitted light as in block 616. When a photocell or photodetector is used as the detector in block 610, the pulsed light is detected by the photocell in block 618. The photocell measures the intensity of the pulsed light in block 620. A spectrum may be generated based on the measured light intensity for different wavelengths of emitted light as in block 622. In particular, the photocell may produce a voltage proportional to the light intensity and the spectrum may be a function of the photocell voltage versus the optical wavelength of the light.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. §1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The above disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description. While various embodiments of the invention have been described, it will be apparent to those of ordinary skill in the art that many more embodiments and implementations are possible within the scope of the invention. Accordingly, the invention is not to be restricted except in light of the attached claims and their equivalents.

We claim:

1. An apparatus for point spectroscopy comprising:
a light source;
an optical beam emitted from the light source that is chopped or pulsed at an optical frequency;
a detector that receives the optical beam from the light source and detects acoustic waves; and
a target material disposed on the detector that generates an acoustic wave on a surface of the detector by reacting to the optical beam incident on the target material, wherein the detector measures vibration from the generated acoustic wave that is induced-as the optical frequency is changed.

2. The apparatus of claim 1 wherein the acoustic wave induces the vibration of the detector.

3. The apparatus of claim 1 wherein the optical frequency corresponds with a resonant frequency of the detector.

4. The apparatus of claim 3 wherein the detector comprises a mechanical resonator, wherein the optical frequency corresponds with a resonant frequency of the mechanical resonator.

5. The apparatus of claim 4 wherein the detector comprises a tuning fork, wherein the resonant frequency corresponds with a resonant frequency of the tuning fork.

6. The apparatus of claim 1 wherein the detector comprises a photocell configured to measure an intensity of the optical beam.

7. The apparatus of claim 1 wherein the target material is coated or covered over the detector.

8. The apparatus of claim 1 wherein the detector comprises a quartz crystal tuning fork and the target comprises a material that is coated on the quartz crystal tuning fork.

9. The apparatus of claim 1 wherein an amplitude of the vibration of the quartz crystal tuning fork is measured as the optical frequency of the pulsed light is varied to generate a spectrum.

10. A system for point spectroscopy comprising:
a source array comprising a plurality of sources that each emit a pulsed light beam at a predetermined frequency;
a detector array comprising a plurality of detectors that each have a predetermined resonant frequency, wherein the resonant frequency for each of the detectors corresponds with the predetermined frequency from at least one of the sources; and
a target material that is disposed on one or more detectors in the array that reacts to the pulsed light beams, wherein a photoacoustic induced vibration of the corresponding detector results from the reaction of the target material to the pulsed light beams.

11. The system of claim 10 wherein the measurement at each of the detectors comprises an acoustic or vibrational measurement generated on the surface of the detector.

12. The system of claim 11 wherein a spectrum of the measurement is generated based on the measured vibrational intensity at the predetermined frequencies of each of the sources.

13. The system of claim 10 wherein the target material is coated or covered on the one or more detectors in the array.

14. The system of claim 10 wherein the source array comprises a plurality of light sources or a single source with a grating that produces individual optical wavelengths corresponding to the detectors in the detector array, further wherein the detector array comprises a mechanical resonator.

15. A method for point spectroscopy comprising:
providing a light source;
chopping light emitted from the light source at a predetermined frequency;
directing the emitted light to a target coated on a detector, wherein the target reacts to the emitted light;
measuring the reaction at the detector to the emitted light, wherein the reaction comprises an acoustic wave that is generated on a surface of the detector; and
measuring each of the reactions at the detector to the emitted light as the chopping frequency is adjusted; and
generating a spectrum of the measured reactions based on a measured vibrational intensity at the chopping frequencies.

16. The method of claim 15 wherein the acoustic wave generation varies as the chopping frequency is adjusted.

17. The method of claim 15 wherein the measuring the reaction comprises measuring the acoustic wave that is generated on the surface of the detector.

18. The method of claim 15 wherein the measurement comprises measuring a photoacoustic induced vibration of the detector as the chopping frequency is adjusted.

19. The method of claim 15 further comprising analyzing the measurements to identify the target.

20. The method of claim 15 wherein the chopping frequency is substantially similar to a resonant frequency of the detector.

\* \* \* \* \*